(12) United States Patent
Wedekind et al.

(10) Patent No.: US 8,993,001 B2
(45) Date of Patent: Mar. 31, 2015

(54) METHODS AND COMPOSITIONS FOR TREATING FELINE HYPERTHYROIDISM

(75) Inventors: Karen Joy Wedekind, St. Peters, MO (US); Dale Allen Fritsch, Topeka, KS (US); Chadwick Everett Dodd, Lawrence, KS (US); Timothy Arthur Allen, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 1228 days.

(21) Appl. No.: 12/162,452

(22) PCT Filed: Jan. 26, 2007

(86) PCT No.: PCT/US2007/061100
§ 371 (c)(1),
(2), (4) Date: Feb. 6, 2009

(87) PCT Pub. No.: WO2007/087623
PCT Pub. Date: Aug. 2, 2007

(65) Prior Publication Data
US 2009/0226540 A1 Sep. 10, 2009

Related U.S. Application Data

(60) Provisional application No. 60/762,479, filed on Jan. 26, 2006.

(51) Int. Cl.
| | | |
|---|---|---|
| A01N 59/12 | (2006.01) | |
| A61K 45/06 | (2006.01) | |
| A23K 1/16 | (2006.01) | |
| A23K 1/175 | (2006.01) | |
| A23K 1/18 | (2006.01) | |
| A61K 31/4164 | (2006.01) | |
| A61K 31/4172 | (2006.01) | |
| A61K 31/513 | (2006.01) | |
| A61K 33/04 | (2006.01) | |
| A61K 33/18 | (2006.01) | |

(52) U.S. Cl.
CPC ............... *A61K 45/06* (2013.01); *A23K 1/1628* (2013.01); *A23K 1/1646* (2013.01); *A23K 1/1758* (2013.01); *A23K 1/1846* (2013.01); *A61K 31/4164* (2013.01); *A61K 31/4172* (2013.01); *A61K 31/513* (2013.01); *A61K 33/04* (2013.01); *A61K 33/18* (2013.01); *Y10S 426/805* (2013.01)
USPC ........................... 424/667; 424/702; 426/805

(58) Field of Classification Search
USPC ................... 426/805; 424/667, 702
See application file for complete search history.

(56) References Cited

U.S. PATENT DOCUMENTS

| | | | |
|---|---|---|---|
| 4,880,112 A * | 11/1989 | Conrad | ........................ 206/216 |
| 5,017,389 A | 5/1991 | Green | |
| 5,084,482 A | 1/1992 | Hirsch et al. | |
| 5,484,623 A | 1/1996 | McLean | |
| 5,885,592 A | 3/1999 | Duan et al. | |
| 6,046,308 A | 4/2000 | Glücksmann | |
| 6,071,415 A | 6/2000 | Frommer et al. | |
| 6,245,364 B1 | 6/2001 | Jones et al. | |
| 7,258,879 B1 | 8/2007 | Hodge et al. | |
| 2003/0077254 A1 | 4/2003 | Ramaekers | |
| 2003/0105114 A1 | 6/2003 | Carpino et al. | |
| 2004/0081743 A1 | 4/2004 | Laflamme et al. | |
| 2005/0058691 A1* | 3/2005 | Wedekind et al. | ............ 424/442 |
| 2005/0064016 A1* | 3/2005 | Wedekind et al. | ............ 424/442 |
| 2005/0171104 A1 | 8/2005 | Rahimi-Ghadim et al. | |
| 2009/0226540 A1 | 9/2009 | Wedekind et al. | |
| 2009/0269416 A1* | 10/2009 | Wedekind et al. | ............ 424/601 |
| 2009/0275505 A1 | 11/2009 | Wedekind | |
| 2010/0068304 A1* | 3/2010 | Wedekind et al. | ............ 424/667 |

FOREIGN PATENT DOCUMENTS

| | | |
|---|---|---|
| RU | 2230458 | 6/2004 |
| WO | WO 97/11703 | 3/1997 |
| WO | 03039562 A | 5/2003 |
| WO | WO 04/112498 | 12/2004 |
| WO | WO-2004/112499 A1 * | 12/2004 |

OTHER PUBLICATIONS

Behrend, "Medical Therapy of Feline Hyperthyroidism", Mar. 1999, Compendium on Continuing Education for the Practicing Veterinarian, vol. 21 No. 3, pp. 234-244.*
Tarttelin. M. F. et al. "Dietary Iodine Level and Thyroid Function in the Cat," Journal of Nutrition. Wistar Institute of Anatomy and Biology, (1994) pp. 2577S-2578S, 124:12,Philadelphia, PA USA p. 2578S, left-hand column, paragraph 1.
Yu, S, et al. "A low-selenium diet increases thyroxine and decreases 3,5,3' triiodothyronine in the plasma of kittens," J. Anim. Physiol. A. Anim. Nutr., (2002) pp. 36-41, 86, Berlin "Diets" p. 37.
"Royal Canin Veterinary Diet," Internet Citation, [Online] XP002301316 Retrieved from the Internet: URL:http://www.walthamusa.com/Learning%20Center/pdf/LP21.pdf>, [retrieved on Oct. 15, 2004] p. 8.
Ranz D et al., "Estimation of Iodine Status in Cats," Journal of Nutrition, Wistar Institute of Anatomy and Biology, (2002) pp. 1751S-1753S, 132:6, the whole document Philadelphia, PA, USA.
Labuc, R.H. et al., "Feline Hyperthyroidism-A Short Review," Australian Veterinary Practitioner, (1986), pp. 139-142, 16:3, Sydney, AU, the whole document.
Board on Agriculture: "Nutrient requirements of cats," Nutrient Requirements of Cats, (1986) p. 18, Iodine.

(Continued)

Primary Examiner — Ali Soroush
(74) Attorney, Agent, or Firm — Thomas M. Hunter

(57) ABSTRACT

Methods for treating feline hyperthyroidism comprising (1) administering to a feline an antithyroid agent in conjunction with feeding the feline a composition comprising from about 0.1 to less than about 1 mg/kg iodine or (2) feeding the feline a composition comprising from about 0.1 to less than about 1 mg/kg selenium on a dry matter basis.

11 Claims, No Drawings

(56) References Cited

OTHER PUBLICATIONS

Trepanier, et al., "Medical Management of Hyperthyroidism," Clinical Techniques in Small Animal Practice, (2006), pp. 22-28, 21:1, Philadelphia, PA, USA, the whole document.
Foster, D.J. et al., "Selenium Status of Cats in Four Regions of the World and Comparison With Reported Incidence of Hyperthyroidism in Cats in Those Regions," American Journal of Veterinary Research, (2001) pp. 934-937, 62:6, p. 936, col. 2, paragraph 3.
International Search Report Dated Nov. 6, 2007.
Anonymous, "Sodium selenate", Life Link, Internet article cited in PCT/US2004/019853 as being retrieved from the Internet on Oct. 13, 2004 (XP002301317); http://www.lifelinknet.com/siteResources/ProductPages/Sodium-Selenate.asp.
Association of American Feed Control Officials (AAFC0), "AAFC0 Cat Food Nutrient Profiles Based on Dry Matter," Official Publication, pp. 132-133 (2002).
Association of American Feed Control Officials (AAFCO), "AAFCO Cat Food Nutrient Profiles Based on Dry Matter," Official Publication, pp. 134-135 (2004).
Brewer, "Nutrition of the Cat", J. Am. Vet. Med. Assoc., 108(10):1179-1182 (1982).
Brown et al., "Thyroid Growth Immunoglobulins in Feline Hyperthyroidism", Thyroid, 2(2):125-130 (1992).
Buffington, "Nutritional Requirements and Feeding Recommendations", The Cat: Diseases and Clinical Management, 2nd Ed., pp. 133-151 (1994).
Court et al., "Identification and concentration of soy isoflavones in commercial cat foods", Am. J. Vet. Res., 63(2): 181-185 (2002).
Divi et at, "Anti-Thyroid Isoflavones from Soybean—Isolation, Characterization, and Mechanisms of Action", Biochemical Pharmacology, 54:1087-1096 (1997).
Doerge et al, "Goitrogenic and Estrogenic Activity of Soy Isoflavones", Environmental Health Perspectives, 110(3):349-353 (Jun. 2002).
Edinboro et al., "Epidemiologic study of relationships between consumption of commercial canned food and risk of hyperthyroidism in cats", JAVMA, 224(6):879-886 (Mar. 2004).
Ferguson, "Update on Diagnosis of Canine Hypothyroidism", Vet. Clin. N. Am. Small Anim. Pract., 24(3)515-539 (1994).
Fox et al., "Electrocardiographic and Radiographic Changes in Cats with Hyperthyroidism: Comparison of Population Evaluated During 1992-1993 vs. 1979-1982", J. Anim. Hosp. Assoc. 35(1):27-31 (1999).
Fradkin et a, "Iodine-induced Thyrotoxicosis", Medicine 62(1):1-20 (1983).
Gerber et al., "Etiopathology of Feline Toxic Nodular Goiter", Vet. Clin. N. Am. Small Anim. Pract. Thyroid Disorders, 24(3).541-565 (May 1994).
Hoffmann et al., "Transdermal Methimazole Treatment in Cats with Hyperthyroidism", J. Feline Med. Surg. 5(2):77-82 (2003).
Holzworth et al., "Hyperthyroidism in the Cat: Ten Cases", J. Am. Vet. Med. Assoc., 176(4):345-353 (Feb. 1980).
Johnson et al., "Iodine content of commercially-prepared cal foods", NZ Vet. J., 40:18-20 (1992).
Kass et al, "Evaluation of Environmental, Nutritional and Host Factors in Cats with Hyperthyroidism", J. Vet. Intern. Med., 13:323:329 (1999).
Kyle et al., "Serum free thyroxine levels in cats maintained on diets relatively high or low in iodine", NZ Vet. J., 42:101-103 (1994).
Laurberg et al., "Environmental Iodine Intake Affects the Type of Nonmalignant Thyroid Disease", Thyroid, 11:457-469 (Nov. 2001).
Laurberg et al., "High incidence of multinodular toxic goiter in the elderly population in low iodine intake area vs. high incidence of Graves' disease in the young in a high iodine intake area: comparative surveys of thyrotoxicosis epidemiology in East-Jutland Denmark and Iceland", J. Internal Med., 229:415-420 (1991).
Martin et al., "Evaluation of dietary and environmental risk factors for hyperthyroidism in cats", J. Am. Vet. Med. Assoc., 217(6)853-856 (Sep. 2000).
Martins et al., "Natural course of iodine-induced thyrotoxicosis (Jodbasedow) in endemic goiter area; A 5 year follow-up", J. Endocrin. Invest., 12;239-244 (1989).
Mason et al., "Determination of Iodine in Urine, Using Epithermal Instrumental Neutron Activation Analysis (EINAA), at the University of Missouri Research Reactor (MURR)", J. Radioanalytical Nucl. Chem., 195(1):57-65 (1995).
McDowell, Iodine. In: Minerals in Animal and Human Nutrition, San Diego: Academic Press, pp. 224-245 (1992).
Mumma et al., "Toxic and protective constituents in pet foods", Am. J. Vet. Res., 47(7):1633-1637 (Jul. 1986).
National Research Council, "No. 13: Nutrient Requirement of Cats Revised 1978", National Academy of Sciences, pp. 10, 18-21, 25-27 (1978).
Nichols et al., "Longitudinal study of iodine in market milk and infant formula via epiboron neutron activation analysis", J. Radioanalytical Nucl. Chem., 236(1-2):65-69 (1998).
Pennington, "A review of iodine toxicity reports", J. Am. Dietetic Assoc., 90(11):1571-1581 (1990).
Peterson et al., "Spontaneous Hyperthyroidism in the Cat" (Abstract), Proceedings of the American College of Veterinary Internal Medicine, 108 (Jul. 1979).
Peterson et al., "Spontaneous Feline Hyperthyroidism" (Abstract), Program of the 62nd Annual Meeting of the Endocrine Society, No. 516, 203 (1980).
Peterson et al., "Propylthiouracil in the Treatment of Feline Hyperthyroidism", J. Am. Vet. Med. Assoc., 179:485-487 (Sep. 1981).
Peterson et al., "Feline Hyperthyroidism: Pretreatment Clinical and Laboratory Evaluation of 131 Cases", J. Amer. Vet. Med. Assoc. 1983(1);103-110 (1983).
Peterson et al., "Comparison of the Disposition of Carbimazole and Methimazole in Clinically Normal Cats", Res. Vet. Sci. 54(3):351-355 (1993).
Peterson et al., "The cat: diseases and clinical management", R.G. Sherding, ed., New York, Churchill Livingstone, 2nd Ed., pp. 1416-1452 (1994).
Robbins et al., *Pathologic Basis of Disease*, 3rd ed., pp. 1203-1204 (1984).
Scarlett et al.. "Feline Hyperthyroidism: A Descriptive and Case-Control Study", Preventive Vet. Med., 6:295-309 (1988).
Schrauzer, "Selenomethionine: A Review of Its Nutritional Significance, metabolism and Toxicity", J. Nutr., 130:1653-1656 (2000).
Slater et al., "Long-Term Health and Predictors of Survival for Hyperthyroid Cats Treated Iodine 131", J. Vet. Intern. Med. 15(1):47-51 (2001).
Smith, "Changes and challenges in feline nutrition", J. Am. Vet. Med. Assoc., 203(10):1395-1400 (Nov. 1993).
Son et al., "Lack of Effect of Soy Isoflavone on Thyroid Hyperplasia in Rats Receiving an Iodine-deficient Diet", Jpn. J. Cancer Res. 92:103-108 (Feb. 2001).
Spate et al., "Determination of Iodine in Human Nails Via Epithermal Neutron Activation Analysis", J. Radioanalytical and Nuclear Chemistry, Articles, vol. 195, No. 1. pp. 21-30 (1995).
Tarttelin et al., "Dietary Iodine Level and Thyroid Function in the Cat", Am. Inst. Nutr. J. Nutr., 124:2577S-2578S (1994).
Tarttelin et al., "Serum free thyroxine levels respond inversely to changes in level of dietary iodine in the domestic cat", NZ Vet. J., 40:66-68 (1992).
Wedekind et al., "Defining the Safe Lower and Upper Limit for Selenium (Se) in Adult dogs" (Abstract), Annual Meeting of Professional Research Scientists on Experimental Biology, New Orleans, Louisiana, USA (Apr. 20-24, 2002).
Wedekind et al., "Current AAFCO and NRC Recommendations for Selenium (Se) Are Too Low for Kittens" (Abstract), FASEBJ 14(4):A295 (2000).
Wedekind et al., "Effect of Varying Selenium (Se) Intake on Thyroid Hormone Metabolism in Dogs" (Abstract), FASEBJ 15(5):A953 (2001).
Wedekind et al., "Bioavailability of Selenium in Petfood Ingredients" (Abstract), Annual Meeting of Professional Research Scientists on Experimental Biology, New Orleans, Louisiana, USA (Apr. 6-9, 1997).

(56) References Cited

OTHER PUBLICATIONS

Wedekind et al., "Determination of the selenium requirement in kittens", J. Anim. Physiol. Anim. Nutr., 87:315-323 (2003).
Wedekind et al., "Selenium in Pet Foods—Is Bioavailability an Issue?", Proceedings, Purina Nutrition Forum: Supplement to Compendium on Continuing Education for the Practicing Veterinarian, 22(9A):17-22 (Sep. 2000).
Wedekind, "The selenium requirement of the puppy", J. Anim. Physiol. Anim. Nutr., 88: 1-8 (2004).
Yang et at., "Endemic selenium intoxication of humans in China", Am. J. Clin. Nutr., 37(5):872-881 (May 1983).
Yang et al., "Studies of Safe Maximal Daily Dietary Se-intake in a Seleniferous Area in China. Part II: Relation Between Se-Intake and the Manifestation of Clinical Signs and Certain Biochemical Alterations in Blood and Urine", J. Trace Elem. Electrolytes Health Dis., 3(3):123-130 (1989).
Belikov V.G., Pharmaceutical Chemistry, Moskow: Vysshaya Shkola, 1993, pp. 43-47.
Chervyakov, D.K., Drugs in Veterinary, Moskow: Kolos, 1977, p.217.
Loginova, N.V., Introduction to Pharmaceutical Chemistry, Minsk: BGU, 2003, p. 216.
Thyrotoxicosis and Hypothyroidism: Evaluation and Management Guidleines of the Am. Assoc. of Clinical Endocrinologists, SMM Endokrinologiya, 2002, p. 26, http://www.airmed.com.au/standart/10.pdf.
Luo et al., 1991, "The Novel Effects of Selenium on Animals," China Feedstuff, pp. 20-23.
Peterson et al., 1988, "Methimazole Treatment of 262 Cats with Hyperthyroidism," J. Vet. Int. Med. 2(3):150-157.
Levander, Selenium. In: Trace Elements in Human and Animal Nutrition; Mertz, W. ed. Orlando, FL: Academic Press Inc., 1986, pp. 209-279.
Simcock at al., "The role of selenium in companion animal health and nutrition", Institute of Food, Nutrition and Human Health, Massey University, Palmerton North, New Zealand 2010, pp. 511-520.
Small Animal Clinical Nutrition: 4th Ed., Hand, Thatcher, Remillard: Rundebush, 2000, pp. 863-868 (Disorders of the Thyroid Gland).
Trepanier et al., "Efficacy and safety of once versus twice daily administration of methimazole in cats with hyperthyroidism". J. Am. Vet. Med. Assoc., 2003, 222(7):954-958.
Yu et al., "A Low-Selenium Diet Increases Thyroxine and Decreases 3,5,3'Triiodothyronine in the Plasma of Kittens", J. Anim. Physiol. a. Anim. Nutr., 2002, 86:36-41.

\* cited by examiner

METHODS AND COMPOSITIONS FOR TREATING FELINE HYPERTHYROIDISM

CROSS-REFERENCE TO RELATED APPLICATION

This application claims priority to U.S. Provisional Application Ser. No. 60/762,479 filed Jan. 26, 2006, the disclosure of which is incorporated herein by reference.

BACKGROUND OF THE INVENTION

1. Field of the Invention

The invention relates generally to methods and compositions for treating hyperthyroidism and particularly to methods and compositions for treating feline hyperthyroidism.

2. Description of the Prior Art

Hyperthyroidism is a relatively common endocrine disorder, particularly in older cats. Typical hyperthyroidism treatments include chronic administration of an anti-thyroid medication, surgical removal of the thyroid glands, and/or radioactive iodine therapy. These treatments are expensive and have their limitations and side effects. For example, as most anti-thyroid medications are administered orally, compliance is often compromised. Surgery requires anesthesia and is not necessarily an option for older felines, particularly felines that suffer from other diseases as well. Radioactive iodine therapy is available only in facilities licensed to use radioactive materials, and requires hospitalization of the felines until their body levels of radioactivity are safe. There is, therefore a need for alternative compositions and methods for treating hyperthyroidism which provide partial or complete relief. The invention provides compositions and methods of treatment that generally address such a need.

SUMMARY OF THE INVENTION

It is, therefore, an object of the present invention to provide methods for treating feline hyperthyroidism.

It is another object of the invention to provide compositions suitable for treating feline hyperthyroidism.

It is another object of the invention to provide articles of manufacture comprising a composition of the invention or two or more ingredients that, when combined together and optionally with additional ingredients that are or are not a part of the article of manufacture, yield a composition of the invention.

It is a further object of the invention to provide means for communicating information about the compositions, methods, and articles of manufacture of the invention.

These and other objects are achieved using compositions that comprise from about 0.1 to less than about 1 mg/kg iodine on a dry matter basis and/or from about 0.1 to less than about 1 mg/kg selenium on a dry matter basis, and, optionally, an antithyroid agent.

Additional and further objects, features, and advantages of the present invention will be readily apparent to those skilled in the art.

DETAILED DESCRIPTION OF THE INVENTION

In one aspect the invention provides compositions suitable for treating hyperthyroidism in a feline. Hyperthyroidism is characterized by hypermetabolism of the thyroid gland and excessive production of the thyroid hormones triiodothyronine ($T_3$) and tetraiodothyronine (thyroxine or $T_4$). Most of $T_3$ and $T_4$ are bound to serum proteins. The portion of $T_3$ and $T_4$ partitioned into serum, and not associated with protein, is called free $T_3$ ($fT_3$) and $T_4$ ($fT_4$). One skilled in the art can accurately diagnose hyperthyroidism in a feline utilizing thyroid function tests, examining clinical signs, and/or observing the animal's response to trial thyroid hormone administration. Thyroid function tests are known to those skilled in the art and include, for example, tests for determining the concentrations of total and free serum $T_3$ and $T_4$, tests for determining the concentration of thyroid stimulating hormone (TSH), and the sodium pertechnetate and $T_3$ suppression tests. See, for example, Small Animal Nutrition, pages 863-868 (2000). Treating hyperthyroidism as used herein includes ameliorating, suppressing, and/or eradicating hyperthyroidism.

In some embodiments, the feline is a companion feline. A companion feline can be a feline kept as a pet. A companion feline can also be a feline from a widely domesticated species, for example, cats (*Felis domesticus*) regardless of whether or not it is kept as a pet. In some embodiments, the feline is an adult feline. An adult feline is a feline of any age after juvenile growth and development has been completed, including senior and geriatric felines. For example, an adult cat typically is one that is from about one year old through the remainder of its life. A senior feline is one of an age at which it is at a risk for suffering from an age-related disease regardless of whether or not the feline shows obvious physical or behavioral signs of aging. For example, a senior cat typically is a cat from about seven to about eleven years old. A geriatric feline is a feline showing signs of aging. For example, a geriatric cat typically is a cat of about twelve years of age and beyond.

In some embodiments, the composition of the invention comprises from about 0.1 to less than about 1 mg/kg iodine on a dry matter basis. In some such embodiments, the composition comprises from about 0.1 to about 0.5 mg/kg iodine on a dry matter basis. In other such embodiments, the composition comprises from about 0.1 to about 0.3 mg/kg iodine on a dry matter basis. In yet other such embodiments, the composition comprises from about 0.15 to about 0.25 mg/kg iodine on a dry matter basis. And in further such embodiments, the composition comprises from, about 0.1 to about 0.2 mg/kg iodine on a dry matter basis. As discussed above, iodine is a constituent of $T_3$ and $T_4$. The thyroid glands actively trap iodine to ensure an adequate supply of thyroid hormones. Iodine as used herein refers to the iodine atom without reference to its molecular or ionic form, and includes iodine present in one or more chemical forms such as, for example, iodide, iodate, and periodate.

In some embodiments, the composition of the invention comprises from about 0.1 to less than about 1 mg/kg selenium on a dry matter basis. In some such embodiments, the composition comprises from about 0.1 to about 0.8 mg/kg selenium on a dry matter basis. In other such embodiments, the composition comprises from about 0.15 to about 0.65 mg/kg selenium on a dry matter basis. In yet other such embodiments, the composition comprises from about 0.4 to about 0.7 mg/kg selenium on a dry matter basis. In further such embodiments, the composition comprises from about 0.3 to about 0.65 mg/kg selenium on a dry matter basis. Selenium has a role in maintaining normal thyroid and iodine metabolism, particularly through the control of the deiodinase enzymes that regulate the conversion of $T_4$ to $T_3$. Selenium as used herein refers to the selenium atom without reference to its molecular or ionic form, and includes selenium present in one or more chemical forms such as, for example, selenide, selenite, and selenate.

In some embodiments, the composition of the invention comprises from about 0.1 to less than about 1 mg/kg iodine on a dry matter basis and from about 0.1 to less than about 1 mg/kg selenium on a dry matter basis. In some such embodiments, the composition comprises from about 0.1 to about 0.5 mg/kg iodine on a dry matter basis and from about 0.1 to about 0.8 mg/kg selenium on a dry matter basis. In other such embodiments, the composition comprises from about 0.1 to about 0.3 mg/kg iodine on a dry matter basis and from about 0.15 to about 0.65 mg/kg selenium on a dry matter basis. In further such embodiments, the composition comprises (1) from about 0.1, about 0.15, or about 0.2 to about 0.25, about 0.3, or about 0.5 mg/kg iodine on a dry matter basis, and (2) from about 0.1, about 0.15, about 0.3, or about 0.4 to about 0.65, about 0.7, or about 0.8 mg/kg selenium on a dry matter basis.

In some embodiments, the composition of the invention comprises a food composition (i.e., the composition comprises one or more food compositions). In some such embodiments, the composition meets the AAFCO's minimum nutrient, level requirements for reproduction or maintenance. See AAFCO Official Publication, pages 137-140 (2005). In other such embodiments, the composition comprises less than the AAFCO's minimum requirements for reproduction or maintenance (e.g., the composition comprises less iodine and/or selenium than the amount recommended by the AAFCO). In some embodiments, the food composition comprises a dry food. In some embodiments, the food composition comprises a semi-moist food. In some embodiments, the food composition comprises a moist food. In some embodiments, the food composition comprises a supplement, treat, snack, or partially or fully edible toy. In some embodiments, the composition comprises a mixture of two or more foods.

In some embodiments, a composition of the invention as described above further comprises an antithyroid agent (i.e., the composition comprises one or more antithyroid agents). An antithyroid agent is a compound, a derivative thereof (e.g., a salt, solvate, or hydrate of the compound), or a composition comprising such compounds and/or derivatives that is used to treat hyperthyroidism. Suitable antithyroid agents include, for example, thioureylenes (e.g., methimazole, propylthiouracil, and carbimazole), aniline derivatives (e.g., sulfonamides), polyhydric phenols (e.g., resorcinol), and lithium salts. In some embodiments, the antithyroid agent comprises a thioureylene. Thioureylenes are five- or six-member thiourea derivatives that block production of thyroid hormones. In some such embodiments, the antithyroid agent comprises the thioureylene methimazole. In other such embodiments, the antithyroid agent comprises the thioureylene propylthiouracil. In further such embodiments, the antithyroid agent comprises the thioureylene carbimazole.

In some embodiments, a composition of the invention comprises a therapeutically-effective amount of an antithyroid agent (i.e., the composition comprises one or more antithyroid agents, and the total amount of the antithyroid agents is a therapeutically-effective amount). A therapeutically-effective or effective amount is an amount that will achieve the goal of treating the targeted condition. Those skilled in the art either know or can determine by routine experimentation how much of an agent or combination of agents to administer to a feline to treat hypothyroidism. For example, one skilled in the art can prepare a composition that, when fed to the feline in a maintenance-sufficient, amount, typically will deliver a therapeutically-effective amount of the agent(s) present in the composition. In some cases, the amount of the antithyroid agent may vary with the stage of treatment. For example, higher doses of an antithyroid agent may be used in the initial stage of treatment (i.e., the therapeutically-effective amount of the particular agent may vary with the stage of the disease). One skilled in the art can prepare compositions of the invention with varying amounts of an antithyroid agent, and then feed those compositions sequentially to deliver the desired amount of antithyroid agent(s) to the feline.

Tables 2 and 3 of U.S. Patent Application Publication No. US 2005/0058691 A1 list the iodine and selenium content of commercially available canned and dry cat foods. The average amounts of selenium in the 28 tested canned foods and 14 tested dry foods were 1.77 and 0.69 mg/kg on a dry matter basis, respectively, with many foods having more than 2 mg/kg. The average amounts of iodine in those foods were 7.83 mg/kg and 2.77 mg/kg on a dry matter basis, respectively, with some foods having more than 30 mg/kg. Thus, the compositions of the invention comprise amounts of iodine and/or selenium that are lower (and in some embodiments, much lower) than the amounts of iodine and selenium in many commercially available foods. Thus, in some embodiments, feeding a composition of the invention to a feline results in restricting the feline's intake of iodine. In other embodiments, feeding a composition of the invention to a feline results in restricting the feline's intake of selenium. In further embodiments, feeding a composition of the invention to a feline results in restricting the feline's intake of both iodine and selenium.

In another aspect, the invention provides a method for preparing a composition of the invention. Such, a composition can be prepared, for example, by combining two or more compositions (including food compositions) or one or more food compositions and additional ingredient(s) such as, for example, an antithyroid agent. A composition of the invention can also be prepared by one or more of the methods discussed in, for example. Small Animal Nutrition, pages 127-146 (2000). To prepare a low selenium-comprising composition of the invention, one can use, for example, a selenium-free mineral mix and ingredients that contain small amounts of selenium such as, for example, potato concentrate, soy concentrate, and soy protein isolate. To prepare a low iodine-comprising composition of the invention, one can, for example, avoid food colorings rich in iodine and can use an iodine-free mineral mix, non-iodized salt, or ingredients that contain small amounts of iodine such as, for example, potato concentrate, soy concentrate, and soy protein isolate.

Iodine and selenium-containing ingredients suitable for preparing a composition of the invention are listed in, for example, table 3 of U.S. Patent Application Publication No. US 2005/0058691 A1. Plant ingredients suitable for preparing a composition of the invention include, for example, soybean meal, corn gluten meal, rice protein isolate, pea protein concentrate, wheat protein concentrate, and wheat protein isolate. Eggs can be used for preparing a composition of the invention as well. Meat (including fish) ingredients suitable for preparing a composition of the invention include, for example, pork liver, beef spleen, beef tongue, pork lung lobes, beef lung, meat protein isolate, deboned turkey, chicken backs, mackerel, oceanfish, and poultry by-product meal.

As discussed above, commercially available cat foods typically contain higher amounts of iodine and selenium than the amounts of iodine and/or selenium in a composition of the invention. Thus, to minimize iodine and/or selenium carryover, before preparing a composition of the invention, it may be desirable to clean the equipment that will be used. For example, to minimize iodine or selenium carryover from an earlier retort or extrusion run, the equipment can be appropriately flushed before a low iodine- and/or low selenium-comprising composition of the invention will be made. In some cases, it may also be desirable to discard the initial portion of a batch to obtain a composition with a consistent concentration of iodine and/or selenium throughout the entire batch.

In a further aspect, the invention provides a method for treating hyperthyroidism in a feline. In some embodiments, the method comprises feeding the feline a composition selected from the compositions of the invention discussed above. One skilled in the art would understand that either a single composition of the invention can be fed to the feline or, alternatively, different compositions can be fed to the feline for varying time intervals.

In some embodiments, the method comprises feeding the feline a composition that comprises from about 0.1 to less than about 1 mg/kg iodine on a dry matter basis. In some such embodiments, the method comprises feeding the feline a composition that comprises from about 0.1 to about 0.5 mg/kg iodine on a dry matter basis. In other such, embodiments, the method comprises feeding the feline a composition that comprises from, about 0.1 to about 0.3 mg/kg iodine on a dry matter basis. In further such embodiments, the method comprises feeding the feline a composition that comprises from about 0.15 to about 0.25 mg/kg iodine on a dry matter basis. In yet further such embodiments, the method comprises feeding the feline a composition that comprises from about 0.1 to about 0.2 mg/kg iodine on a dry matter basis.

In some embodiments, the method comprises feeding the feline a composition that comprises from about 0.1 to less than about 1 mg/kg selenium on a dry matter basis. In some such embodiments, the method comprises feeding the feline a composition that comprises from about 0.1 to about 0.8 mg/kg selenium on a dry matter basis. In other such embodiments, the method comprises feeding the feline a composition that comprises from about 0.15 to about 0.65 mg/kg selenium on a dry matter basis. In further such embodiments, the method comprises feeding the feline a composition that comprises from about 0.4 to about 0.7 mg/kg selenium on a dry matter basis. In yet further such embodiments, the method comprises feeding the feline a composition that comprises from about 0.3 to about 0.65 mg/kg selenium on a dry matter basis.

In some embodiments, the method comprises feeding the feline a composition that comprises from about 0.1 to less than about 1 mg/kg iodine on a dry matter basis and from about 0.1 to less than about 1 mg/kg selenium on a dry matter basis. In some such embodiments, the method comprises feeding the feline a composition that comprises from about 0.1 to about 0.5 mg/kg iodine on a dry matter basis and from about 0.1 to about 0.8 mg/kg selenium on a dry matter basis. In other such embodiments, the method comprises feeding the feline a composition that comprises from about 0.1 to about 0.3 mg/kg iodine on a dry matter basis and from about 0.15 to about 0.65 mg/kg selenium, on a dry matter basis. In further such embodiments, the method comprises feeding the feline a composition that comprises (1) from about 0.1, about 0.15, or about 0.2 to about 0.25, about 0.3, or about 0.5 mg/kg iodine on a dry matter basis, and (2) from about 0.1, about 0.15, about 0.3, or about 0.4 to about 0.65, about 0.7, or about 0.8 mg/kg selenium on a dry matter basis.

In some embodiments, the method for treating hyperthyroidism of the invention comprises administering to the feline an antithyroid agent in conjunction with feeding the feline a composition that comprises from about 0.1 to less than about 1 mg/kg iodine on a dry matter basis. "Administering" means that the antithyroid agent is introduced in a suitable dosage form into the feline by a suitable administration route, for example, orally, topically, or parenterally. The term "in conjunction" means that the antithyroid agent is administered to the feline either together with a composition of the invention or separately from the composition at the same or different frequency via the same or different administration route and either at about the same time as the composition or periodically. "About at the same time" generally means that an agent is administered when a composition, of the invention is fed to the feline or within about 72 hours of feeding the composition to the feline. "Periodically" generally means that an agent is administered to a feline following a dosage schedule suitable for administering the agent while a composition of the invention is fed to the feline routinely as appropriate for that feline. Thus, the term "in conjunction" specifically includes situations when an agent is administered to a feline for a prescribed period of time while a composition of the invention is fed to the feline for a much longer period of time (e.g., for life). If more than one agent is administered to a feline, the dosage form and route of administration for each agent may vary. In addition, as discussed above, one composition of the invention may be substituted with another composition of the invention while a specific agent is administered to the feline. In some such embodiments, the method comprises administering to the feline an antithyroid agent in conjunction with feeding the feline a composition that comprises from about 0.1 to about 0.5 mg/kg iodine on a dry matter basis. In other such embodiments, the method comprises administering an antithyroid agent in conjunction with feeding the feline a composition that comprises from about 0.1 to about 0.3 mg/kg iodine on a dry matter basis. In further such embodiments, the method comprises administering an antithyroid agent in conjunction with feeding the feline a composition that comprises from about 0.15 to about 0.25 mg/kg iodine on a dry matter basis. In yet further such embodiments, the method comprises administering to the feline an antithyroid agent in conjunction with feeding the feline a composition that comprises from about 0.1 to about 0.2 mg/kg iodine on a dry matter basis.

In some embodiments, the method for treating hyperthyroidism of the invention comprises administering to the feline an antithyroid agent in conjunction, with feeding the feline a composition that comprises from about 0.1 to less than, about 1 mg/kg selenium on a dry matter basis. In some such embodiments, the method comprises administering an antithyroid agent in conjunction with feeding the feline a composition that comprises from about 0.1 to about 0.8 mg/kg selenium on a dry matter basis. In other such embodiments, the method comprises administering an antithyroid agent in conjunction with feeding the feline a composition that comprises from about 0.15 to about 0.65 mg/kg selenium on a dry matter basis. In further such embodiments, the method comprises administering an antithyroid agent in conjunction with feeding the feline a composition that comprises from about 0.4 to about 0.7 mg/kg selenium on a dry matter basis. In yet further such embodiments, the method comprises administering an antithyroid agent in conjunction with feeding the feline a composition that comprises from about 0.3 to about 0.65 mg/kg selenium on a dry matter basis.

In some embodiments, the method the method for treating hyperthyroidism of the invention comprises administering to the feline an antithyroid agent in conjunction with feeding the feline a composition that comprises from about 0.1 to less than about 1 mg/kg iodine on a dry matter basis and from about 0.1 to less than about 1 mg/kg selenium on a dry matter basis. In some such embodiments, the method comprises administering an antithyroid agent in conjunction with feeding the feline a composition that comprises from about 0.1 to about 0.5 mg/kg iodine on a dry matter basis and from about 0.1 to about 0.8 mg/kg selenium on a dry matter basis. In other such embodiments, the method comprises administering an antithyroid agent in conjunction with feeding the feline a composition that comprises from about 0.1 to about 0.3 mg/kg iodine on a dry matter basis and from about 0.15 to about 0.65 mg/kg selenium on a dry matter basis. In further such embodiments, the method comprises administering an antithyroid agent in conjunction with feeding the feline a composition that comprises (1) from about 0.1, about 0.15, or about 0.2 to about 0.25, about 0.3, or about 0.5 mg/kg iodine on a dry matter basis, and (2) from about 0.1, about 0.15, about 0.3, or about 0.4 to about 0.65, about 0.7, or about 0.8 mg/kg selenium on a dry matter basis.

As discussed in the context of the compositions of the invention, the antithyroid agents suitable for the methods of treatment discussed above include, for example, thioureylenes, aniline derivatives, polyhydric phenols, and lithium salts. In some embodiments, the method comprises administering to the feline an antithyroid agent that comprises a thioureylene. In some embodiments, the method comprises administering an antithyroid agent comprising methimazole. In some embodiments, the method comprises administering to a feline an antithyroid agent comprising propylthiouracil. In some embodiments, the method comprises administering an antithyroid agent comprising carbimazole. In some embodiments, the method comprises administering a therapeutically-effective amount of an antithyroid agent in conjunction with feeding the feline a composition of the invention. In some embodiments, the composition fed to a feline comprises the antithyroid agent administered to the feline. In some such embodiments, the method comprises feeding the feline a composition of the invention that comprises a therapeutically-effective amount of an antithyroid agent. Antithyroid agents can be administered, for example, in the form of salts derived from inorganic or organic acids. Depending on the particular compound, a salt of the compound may be advantageous due to one or more of the salt's physical properties, for example, enhanced pharmaceutical stability in differing temperatures and humidities, or a desirable solubility in water or oil. The salt preferably is a pharmaceutically-acceptable salt.

The preferred total daily dose of the antithyroid agent (administered in single or divided doses) is typically from about 0.001 to about 100 mg/kg body weight, more preferably from about 0.01 to about 30 mg/kg body weight, and even more preferably from about 0.01 to about 10 mg/kg body weight. Dosage unit compositions can contain such amounts and submultiples thereof to make up the daily dose. In many instances, the administration of the antithyroid agent will be repeated a plurality of times. Multiple doses per day typically may be used to increase the total daily dose, if desired. Factors affecting the preferred dosage regimen include, for example, the age, weight, and condition of the feline; the severity of the disease; the route of administration; pharmacological considerations, such as the activity, efficacy, pharmacokinetic, and toxicology profiles of the particular antithyroid agent used; whether a drug delivery system is utilized; and whether the antithyroid agent is administered as part of a drug combination. Thus, the dosage regimen can vary widely, and therefore, can differ from the preferred dosage regimen discussed above.

The methods of treatment of the invention are convenient and easy to practice. In some embodiments, it is sufficient to feed a composition of the invention to a feline diagnosed with hyperthyroidism. In some such embodiments, the composition does not contain any antithyroid agents nor are such agents administered to the feline in conjunction with feeding the feline the composition. Thus, such methods provide a cost-effective alternatives to treatment with antithyroid agents. In addition, such methods do not cause the side effects attributed to treatment with antithyroid agents, for example, kidney damage. Finally, such methods result in better compliance because one need only feed a feline a composition of the invention rather than administer, for example, an oral or topical antithyroid drug. As discussed above, in some embodiments, the methods of treatment of the invention comprise feeding the feline a composition comprising an antithyroid agent. Such methods of treatment are more convenient and easier to practice because they eliminate the need for, for example, oral or topical administration of antithyroid agents. In some embodiments, the methods of treatment of the invention allow for administering less antithyroid agent than would be administered in a drug only treatment because the administration of an antithyroid agent in conjunction with feeding the feline a composition of the invention results in a synergistic cooperation between the antithyroid agent administered to the feline and the composition of the invention fed to the feline. In addition, one skilled in the art would know that either a single composition of the invention can be fed to the feline or that different compositions of the invention can be fed to the feline for varying time intervals.

In a further aspect, the invention provides a use of a composition of the invention as discussed above to prepare a medicament for treating hyperthyroidism in a feline. The medicament may also comprise one or more conventional pharmaceutically acceptable carriers, adjuvants, and/or vehicles (together referred to as excipients).

In a further aspect, the invention provides a use of iodine and optionally selenium to prepare a composition of the invention (as discussed above) to treat hyperthyroidism in a feline.

In some embodiments, the invention provides a use of iodine to prepare a composition that comprises from about 0.1 to less than about 1 mg/kg iodine on a dry matter basis and, optionally, an anti-thyroid agent. The composition is used to treat hyperthyroidism in a feline. In some such embodiments, the invention provides a use of iodine to prepare a composition that comprises from about 0.1 or about 0.15 to about 0.2, about 0.25, about 0.3, or about 0.5 mg/kg iodine on a dry matter basis and, optionally, an antithyroid agent to treat hyperthyroidism in a feline. In some embodiments, the composition comprises a food composition.

In some embodiments, the invention provides a use of selenium to prepare a composition that comprises from about 0.1 to less than about 1 mg/kg selenium on a dry matter basis and, optionally, an anti-thyroid agent. The composition is used to treat hyperthyroidism. In some such embodiments, the invention provides a use of selenium to prepare a composition to treat hyperthyroidism that comprises from about 0.1, about 0.15, about 0.3, or about 0.4 to about 0.65, about 0.7, or about 0.8 mg/kg selenium on a dry matter basis and, optionally, an antithyroid agent. In some embodiments, the composition comprises a food composition.

In some embodiments, the invention provides a use of iodine and selenium to prepare a composition that comprises from about 0.1 to less than about 1 mg/kg iodine on a dry matter basis, from about 0.1 to less than about 1 mg/kg selenium on a dry matter basis, and, optionally, an anti-thyroid agent. The composition is used to treat hyperthyroidism. In some such embodiments, the invention provides for use of iodine and selenium to prepare a composition to treat hyperthyroidism that comprises from about 0.1, about 0.15, or about 0.2 to about 0.25, about 0.3, or about 0.5 mg/kg iodine on a dry matter basis, from about 0.1, about 0.15, about 0.3, or about 0.4 to about 0.65, about 0.7, or about 0.8 mg/kg selenium on a dry matter basis, and, optionally, an antithyroid agent. In some embodiments, the composition comprises a food composition.

In a further aspect the invention provides an article of manufacture, for example, a kit for treating hyperthyroidism in a feline that comprises a composition of the invention. In some embodiments, the kit further comprises an antithyroid agent (i.e., the kit comprises one or more antithyroid agents). In some embodiments, the kit can further comprise instructions for one or more of (1) feeding the composition to a feline, (2) administering an antithyroid agent to a feline in conjunction with feeding the feline the composition, (3) treating hyperthyroidism in a feline by feeding the feline the composition, and (4) treating hyperthyroidism in a feline by administering to the feline an antithyroid agent in conjunction with feeding the feline the composition.

In a further aspect, the invention provides an article of manufacture, for example, a kit for treating hyperthyroidism in a feline that comprises two or more ingredients that, when combined together and optionally with additional ingredients that are not a part of the kit, yield a composition of the invention. One of the two or more ingredients that are to be combined can be, for example, iodine or a derivative thereof or a composition comprising iodine or the iodine derivative(s). Another one of the two or more ingredients that are to be combined can be, for example, selenium or a derivative thereof or a composition comprising selenium or the selenium derivative(s). Yet another one of the two or more ingredients that are to be combined can be, for example, a food composition. If, to prepare a composition, additional ingredients that are not a part of the kit are needed, the kit provides instructions about those ingredients. In some embodiments, the kit further comprises an antithyroid agent. In some embodiments, the kit further comprises instructions for one or more of (1) preparing a composition of the invention by combining the two or more ingredients and, optionally, additional ingredients that are not a part of the kit, (2) feeding the composition to a feline to, for example, treat hyperthyroidism, (3) administering an antithyroid agent to the feline in conjunction with feeding the feline the composition, (4) treating hyperthyroidism in a feline by feeding the feline a composition of the invention, and (5) treating hyperthyroidism in a feline by administering to the feline an antithyroid agent in conjunction with feeding the feline the composition.

In some embodiments, the kit comprises in separate containers in a single package or in separate containers in a virtual package, as appropriate, a composition of the invention or two or more ingredients, that, when combined together and optionally with additional ingredients that are not a part of the kit, yield a composition of the invention, and instructions for one or more of (1) feeding the composition to a feline, (2) preparing a composition of the invention by combining the two or more ingredients and, optionally, additional ingredients that are not a part of the kit, (3) treating hyperthyroidism in a feline by feeding the feline the composition, (4) administering an antithyroid agent to the feline in conjunction with feeding the feline the composition, and (5) treating hyperthyroidism in a feline by administering to the feline an antithyroid agent in conjunction with feeding the feline the composition. The term "single package" generally means that the components of a kit are physically associated in or with one or more containers and considered as a unit of manufacture, distribution, sale, or use. Containers include, for example, bags, boxes, bottles, shrink wrap packages, stapled or otherwise fixed components, or combinations thereof. A single package can be, for example, containers or individual food compositions physically associated such that they are considered a unit for manufacture, distribution, sale, or use. The term "virtual package" generally means that the components of a kit are associated by directions on one or more physical or virtual kit components instructing the user how to obtain additional components, for example in a bag containing one component and directions instructing the user to go to a website, contact a recorded message, view a visual message, or contact a caregiver to obtain instructions on how to use the kit. When the kit comprises a virtual package, the kit comprises one or more physical kit components and instructions in a virtual environment.

In some embodiments, the kit comprises in separate containers in a single package or in separate containers in a virtual package, as appropriate a composition comprising from about 0.1 to less than about 1 mg/kg iodine on a dry matter basis and/or from about 0.1 to less than about 1 mg/kg selenium on a dry matter basis, and, optionally, an antithyroid agent, or two or more ingredients, that, when combined together and optionally with additional ingredients that are or are not a part of the kit, yield a composition comprising from about 0.1 to less than about 1 mg/kg iodine on a dry matter basis and/or from about 0.1 to less than about 1 mg/kg selenium on a dry matter basis, and, optionally, an antithyroid agent, and one or more of (1) instructions for feeding the composition to the feline, (2) instructions for preparing the composition by combining the two or more ingredients, (3) instructions for treating hyperthyroidism in a feline by feeding the feline the composition, (4) one or more antithyroid agents, (5) instructions for administering an antithyroid agent to the feline in conjunction with feeding the feline the composition, and (6) instructions for treating hyperthyroidism in a feline by administering to the feline an antithyroid agent in conjunction with, feeding the feline the composition. In some embodiments, the two or more ingredients combined to prepare a composition of the invention comprise one or more of (1) iodine, (2) a composition comprising iodine, (3) selenium, (4) a composition comprising selenium, (5) a composition comprising iodine and selenium, and (6) a composition suitable for consumption by a feline.

In a further aspect, the invention provides a means for communicating information about or instructions for one or more of (1) using a composition of the invention, to treat hyperthyroidism in a feline, (2) treating hyperthyroidism in a feline by administering to the feline an antithyroid agent in conjunction with feeding the feline a composition of the invention, and (3) using a kit of the invention for treating hyperthyroidism in a feline. The means for communicating information comprises a document, digital storage media, optical storage media, audio presentation, or visual display containing the information or instructions. In some embodiments, the communicating means comprises a document, digital storage media, optical storage media, audio presentation, or visual display containing the information or instructions. Preferably, the communication means is a displayed web site or a brochure, product label, package insert, advertisement, or visual display containing such information or instructions. Useful information or instructions include, for example, (1) information and instructions how to use a composition, method, or kit of the invention and (2) contact information for animal caregivers if they have a question about the invention and its uses.

In some embodiments, the invention provides a means for communicating information, about or instructions for one or more of (1) treating hyperthyroidism in a feline by feeding the feline a composition comprising from about 0.1 to less than about 1 mg/kg iodine on a dry matter basis and/or from about 0.1 to less than about 1 mg/kg selenium on a dry matter basis, and, optionally, an antithyroid agent, (2) treating hyperthyroidism in a feline by administering to the feline an antithyroid, agent in conjunction with feeding the feline a composition comprising from about 0.1 to less than about 1 mg/kg iodine on a dry matter basis and/or from about 0.1 to less than about 1 mg/kg selenium on a dry matter basis, (3) using a kit of the invention, and (4) using selenium and/or iodine to prepare a composition for treating hyperthyroidism in a feline that comprises from about 0.1 to less than about 1 mg/kg iodine on a dry matter basis and/or from about 0.1 to less than about 1 mg/kg selenium on a dry matter basis, and, optionally, an antithyroid agent. The means for communicating information comprises a document, digital storage media, audio presentation, or visual display containing the information or instructions. In some such embodiments, the means for communicating information, comprises a brochure, product label, package insert, advertisement, displayed web site, or visual display.

All percentages expressed herein are by weight of the composition on dry matter basis unless specifically stated otherwise. The term "dry matter basis" means that an ingredient's concentration in a composition is measured after any moisture in the composition is removed.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

EXAMPLES

The invention can be further illustrated by the following examples, although it will be understood that the examples are included merely for purposes of illustration and are not intended to limit the scope of the invention unless otherwise specifically indicated.

Example 1

Examples 1 illustrates the effect of the compositions of the invention on treating hyperthyroidism in cats.

Food B1 was formulated as a dry cat food containing 0.6% selenium on a dry matter basis. Food B1 comprised soybean meal, corn gluten meal, poultry meal, and pork meat protein isolate as the protein ingredients, and was formulated with both iodized and non-iodized salt but no selenomethionine and selenium. The average moisture content was 6.6% on a dry matter basis, the average protein content was 33.7% on a dry matter basis, and the average iodine content was 0.38 mg/kg on a dry matter basis (ten samples were taken for iodine analysis, and the iodine content of those samples varied from 0.27 to 0.60 mg/kg on a dry matter basis).

Food B2 was formulated as a wet cat food containing 0.6% selenium on a dry matter basis. It comprised soybean meal, pork lungs, chicken, and pork liver as the protein ingredients. No source of iodine was intentionally added to food B2. No selenomethionine or selenium salts were added to food B1. The average moisture content for those samples was 78.2% on a dry matter basis, the average protein content was 33.2% on a dry matter basis, and the average iodine content was 0.21 mg/kg on a dry matter basis (ten samples were taken for iodine analysis, and the iodine content of those samples varied from 0.14 to 0.27 mg/kg on a dry matter basis).

Food B1 and food B2 were mixed in a 1:1 ratio, thus resulting in food B. A group of five cats diagnosed with hyperthyroidism was fed food B for six weeks. Another five cats diagnosed with hyperthyroidism were given 2.5 mg methimazole orally once a day for six weeks while they were fed food B. Eight cats diagnosed with hyperthyroidism were given 2.5 mg methimazole orally once a day for six weeks while they were fed a commercially available cat food. The thyroid hormone profiles and serum chemistries of all cats were measured at zero, two, four, and six weeks. All cats enrolled in the study had elevated total $T_4$ and/or free $T_4$, with the majority of the cats exhibiting one or more clinical signs associated with hyperthyroid disease (e.g., weight loss, heart murmur/tachycardia, unkempt hair coat, thyroid gland enlargement, increased appetite, vomiting, increased activity, diarrhea, polyuria/polydipsia, aggressiveness, and panting). The results from the study are presented in Tables 1 and 2.

TABLE 1

Change in Serum Total $T_4$ Levels

| Treatment | Change in Serum Total $T_4$ Levels (nmol/L) |
|---|---|
| Methimazole | −20.3 |
| Food B | −31.5 |
| Methimazole + Food B | −42.2 |

TABLE 2

Change in Serum Creatinine Levels

| Treatment | Change in Serum Creatinine Levels (mg/dL) |
|---|---|
| Methimazole | +0.46 |
| Food B | −0.08 |
| Methimazole + Food B | −0.03 |

Treatment with 2.5 mg methimazole administered orally once daily for six weeks resulted in a decrease in serum total $T_4$ concentration and in an increase in serum creatinine concentration (serum creatinine was a bit higher than the 0.8-1.8 mg/dL normal creatinine concentration range). Although this treatment was effective (the total $T_4$ concentration was lowered although it did not reach the normal total $T_4$ concentration range of 10-55 nmol/dL), it may cause or exacerbate kidney disease, and may therefore be unsuitable for treating hyperthyroidism in cats with renal insufficiency.

Feeding food B resulted in a greater decrease in serum total $T_4$ concentration, than treatment with 2.5 mg methimazole alone (although the total $T_4$ concentration was still a bit higher than the normal total $T_4$ concentration range), it also resulted in a decrease in serum creatinine concentration (with creatinine concentration falling within the normal creatinine range). Feeding food B is a more effective treatment for hyperthyroidism than administering 2.5 mg methimazole alone. Feeding food B does not result in the side effects associated with methimazole treatment. Food B is also suitable for felines suffering from or susceptible to developing renal insufficiency.

Administering 2.5 mg methimazole while feeding food B resulted in the greatest decrease in serum total $T_4$ concentration. That decrease in serum total $T_4$ concentration was higher than the corresponding decrease for treatment with methimazole only with $T_4$ falling within the normal total $T_4$ concentration range, indicating that there is a synergism between the action of food B and the antithyroid agent. Administering methimazole in conjunction with feeding food B also resulted in a decrease in serum creatinine concentration (with serum creatinine concentration within the normal range), indicating that the combination is suitable for felines with or susceptible to developing renal insufficiency. Treating hyperthyroidism with methimazole typically involves administering a total of 5 mg methimazole orally (2.5 mg twice a day). The above results demonstrate that administering methimazole in conjunction with feeding food B allows for lowering the amount of the antithyroid drug, thus improving compliance, lowering treatment cost, and/or minimizing side effects.

Example 2

Examples 2 illustrates the effect of the compositions of the invention on treating hyperthyroidism in cats.

Fifteen cats diagnosed with hyperthyroidism were fed food B (from Example 1) for twelve weeks. Eleven cats diagnosed with hyperthyroidism were fed a commercially available cat food (i.e., control food) for twelve weeks. The thyroid hormone profiles and serum chemistries of all cats were measured at zero, two, four, six, and twelve weeks. All cats enrolled in the study had elevated total $T_4$ and/or free $T_4$, with the majority of the cats exhibiting one or more clinical signs associated with hyperthyroid disease. The results from this study are presented in Tables 3 and 4.

TABLE 3

Change in Serum Total $T_4$ Levels

| Treatment | Change in Serum Total $T_4$ Levels (nmol/L) |
|---|---|
| Control Food | +6.5 |
| Food B | −50.4 |

TABLE 4

Change in Serum Creatinine Levels

| Treatment | Change in Serum Creatinine Levels (mg/dL) |
|---|---|
| Control Food | +0.282 |
| Food B | −0.277 |

Feeding control food for twelve weeks resulted in an increase in both serum total $T_4$ and serum creatinine concentrations (with the total $T_4$ concentration above the normal, range and the creatinine concentration within the normal range). Feeding food B for twelve weeks resulted in a decrease in both serum total $T_4$ and serum creatinine concentrations (with both total $T_4$ and creatinine concentrations falling within the normal ranges).

In the specification, there have been disclosed typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A method of treating hyperthyroidism in a felin in need thereof comprising administering to the feline methimazole in conjunction with feeding the feline a composition comprising from about 0.1 to less than about 1 mg/kg iodine on a dry matter basis and about 0.1 to about 1 mg/kg selenium on a dry matter basis.

2. The method of claim 1 wherein a therapeutically-effective amount of methimazole is administered to the feline.

3. The method of claim 1 wherein the composition comprises from about 0.1 to about 0.5 mg/kg iodine.

4. The method of claim 1 wherein the composition comprises from about 0.1 to about 0.3 mg/kg iodine.

5. The method of claim 1 wherein the composition comprises from about 0.1 to about 0.8 mg/kg selenium on a dry matter basis.

6. The method of claim 1 wherein the composition comprises from about 0.15 to about 0.65 mg/kg selenium on a dry matter basis.

7. The method of claim 1 wherein the composition comprises from about 0.1 to about 0.5 mg/kg iodine on a dry matter basis and from about 0.1 to about 0.8 mg/kg selenium on a dry matter basis.

8. The method of claim 1 wherein the composition comprises from about 0.1 to about 0.3 mg/kg iodine on a dry matter basis and from about 0.15 to about 0.65 mg/kg selenium on a dry matter basis.

9. The method of claim 1 wherein the feline is a cat.

10. The method of claim 1 wherein the composition is a food composition.

11. The method of claim 1 wherein the composition fed to the feline comprises methimazole administered to the feline.

* * * * *